United States Patent [19]

Aichinger

[11] 4,197,648
[45] Apr. 15, 1980

[54] METHOD AND APPARATUS FOR PRODUCING A BEND OF SQUARE STEEL WIRE

[76] Inventor: Roswitha Aichinger, Schlossgartenweg 5, Munich, Fed. Rep. of Germany

[21] Appl. No.: 887,305

[22] Filed: Mar. 16, 1978

[30] Foreign Application Priority Data

Mar. 17, 1977 [DE] Fed. Rep. of Germany ....... 2711688

[51] Int. Cl.² .............................................. A61C 7/00
[52] U.S. Cl. ..................................................... 433/3
[58] Field of Search ..................... 140/117, 123; 32/66

[56] References Cited

U.S. PATENT DOCUMENTS

| | | | |
|---|---|---|---|
| 1,991,047 | 2/1935 | Boyd et al. | 32/14 A |
| 2,474,463 | 6/1949 | Burrell | 140/123 |

Primary Examiner—Robert Peshock
Attorney, Agent, or Firm—Harness, Dickey & Pierce

[57] ABSTRACT

A method for producing a bend comprising a plurality of curvatures of square steel wire for tooth regulation by means of a loop bending pliers, wherein the wire is secured against torsion about its longitudinal axis in a holding device during curving. This is done by a wire holder having a guide bore which is open at both ends and the cross sectional outline of which is adapted exactly to the cross sectional outline of the wire.

9 Claims, 2 Drawing Figures

METHOD AND APPARATUS FOR PRODUCING A BEND OF SQUARE STEEL WIRE

FIELD OF THE INVENTION

The invention relates to a method of and an apparatus for producing a bend comprising various curvatures of square steel wire by means of a loop bending pliers, used in orthodontia, i.e. the elimination of irregularities of the teeth by means of fixed devices.

BACKGROUND OF THE INVENTION

In orthodontia steel wires of the kind in question are applied in such manner as to insert them under bias in so-called band fasteners which in turn are welded on to rigid bands, preferably steel bands. The steel bands are adapted accurately to the tooth to be regulated and cemented to the same so as to exert a constant directed action of force on the tooth. Initially it was preferred to bend steel wires of circular cross section. Yet that did not permit sufficiently firm fixation of the bend in the band fasteners. Particularly, it was not possible with wires having a circular cross section to transmit a torque about the longitudinal axis of the wire to the band fastener or to the tooth. Therefore, the general practice went over to forming the bends from square wires. Thus accurate fitting of the square bend in the respective band fastener can be obtained and from the bend a torque about the longitudinal wire axis can be transmitted to the fastener, the band, and thus to the respective tooth. Transmission of the torsional moment may be effected either by twisting the square wire with such aim when producing the bend that a respective restoring moment will result upon insertion in the fasteners provided. In this case fasteners having their square recesses oriented in the same way can be used for all bands. Yet it is also possible to transmit a torsional moment by not pre-twisting the square wire anywhere but instead giving the square recesses in the fasteners different inclinations in accordance with the desired moment to be transmitted to the tooth. In both cases the effect obtained is the same, namely that the bend is biased by a torsional moment at the location of its connection to the band fastener and that the moment of reaction thereof is transmitted to the tooth.

When making the bends which must be formed by hand by the orthodontist himself for each individual case, it is particularly difficult to obtain exactly the desired torsion of the square wire or, when using fasteners with differently inclined recesses, to avoid any twisting at all of the square wire since an undesired twist in the square wire would cause a wrong action of force on the respective tooth. The situation is especially serious because a permanent torsion of the square wire once made cannot be undone, which means that a single error made in curving the bend makes it necessary to discard the bend as waste. So far it has been attempted to avoid any such bending errors by developing special loop bending pliers. These pliers are of very intricate shape and thus very complicated to produce with all the corresponding high costs. Although the problem explained above of avoiding undesired twisting of the square wire has been known for many years, perhaps even for decades, and although attempts have been made for the same length of time to solve the problem by correspondingly designed special pliers, it has not been possible to provide a tool which would enable the orthodontist to make the bends in question without difficulty. Rather, it showed that even when using very expensive special pliers, the production of exactly the desired shape of the bend was more or less a question of luck.

SUMMARY OF THE INVENTION

It is therefore the object of the instant invention to provide a method of and an apparatus for producing bends of the kind specified, which will overcome the difficulties explained above.

It is also an object of the instant invention to provide a method and apparatus permitting the production of bends exactly in accordance with the desired shape.

Another object of the invention is to provide a method and apparatus adapted to achieve the foregoing without having to put up with unacceptable large amounts of waste.

These and other objects which will become apparent as the specification proceeds are met, in accordance with the invention, in that during the formation of the bend the wire is secured against torsion about its longitudinal axis in a holding device. By virtue of the alignment of the lateral faces of the wire in space, in accordance with the invention, the orthodontist may readily give the square wire the desired shape by means of a loop bending pliers, without running the risk of creating uncontrolled twists. Preferably the wire is secured against torsion about its longitudinal axis by being guided in a guide bore, the cross sectional outline of which is exactly adapted to the outline of the square wire. This makes it possible to pull such wire ends out of the guide bore in each instance as are needed for the respective bend to be made. Any uncontrolled actions of force on a longer section of the wire thus are definitely avoided. As soon as a bending operation at a certain location of the wire has been terminated, the wire is drawn out of the guide bore by such a length that the location at which the next bend is to be formed has just left the guide bore so that the curving of the wire at this location again is effected with accurate alignment in space of the lateral faces of the square wire.

In accordance with the invention an apparatus for carrying out the method described is to be characterized by a wire holder having a guide bore which is open at both ends and the cross sectional outline of which is exactly adapted to the cross sectional outline of the wire. The square wires which are available in straight pieces as semi-finished goods can be pushed through the guide bore of the wire holder in a manner so that wire ends just of the length needed for the bending operation project from one end of the guide bore.

In order to warrant the most accurate guidance of the wire in the guide bore and, on the other hand, permit longitudinal displacement of the wire in the guide bore without having to apply too much force, preferably the tolerance between wire and bore is so selected as to provide a sliding fit.

In further development of the invention it is suggested that the outer shape of the wire holder be prismatic and taper toward one end. This shape not only makes it possible to grasp the wire safely at its outer lateral faces but also permits unobstructed working in the direct vicinity of the end of the guide bore. In accordance with another embodiment of the invention the length of the wire holder is to be approximately a hundred times the greater length of the wire cross section, while its height and width are to correspond to approximately ten to twenty times the greatest edge length of the wire cross section. These dimensions afford optimum size of the wire holder so that sufficiently firm support with respect to the bending tool, namely the loop bending pliers is guaranteed between two fingers of a hand. Furthermore, the wire holder has very little weight and, at the same time, it can be handled easily because of its small dimensions.

In accordance with a further modification of the invention it is suggested that the wire holder be made from synthetic resin or a similar non-deformable plastic. Such a material is particularly well suited for the wire holder as it permits the easiest manufacture of the wire holder by casting it around a sample wire. Finally, the use of such material also makes it possible to shape the outside of the wire holder so as to conform to any individually desired handle configuration. However, it is likewise possible to make the wire holder from any suitable metal.

Another embodiment of the invention provides for a metal insert at the tapering end of the wire holder for guidance of the square wire. Using a metal guide has the advantage that wear at the guide bore which could occur particularly at the opening because of the increased action of force through the square wire, is practically excluded. Consequently, uniform exact guidance of the square wire is warranted over a long period of time.

The guiding length of the metal insert preferably is to correspond to eight to twelve times the greater edge length of the wire cross section. It proved that the guide length thus obtained of a metal guide insert is the optimum because the square wire is guided very accurately and, at the same time, there is only little friction between the wire and the guide bore.

BRIEF DESCRIPTION OF THE DRAWING

The invention will be described further, by way of example, with reference to the accompanying drawing, in which.

DETAILED DESCRIPTION OF THE PREFERRED EMBODIMENT

Figure 1:
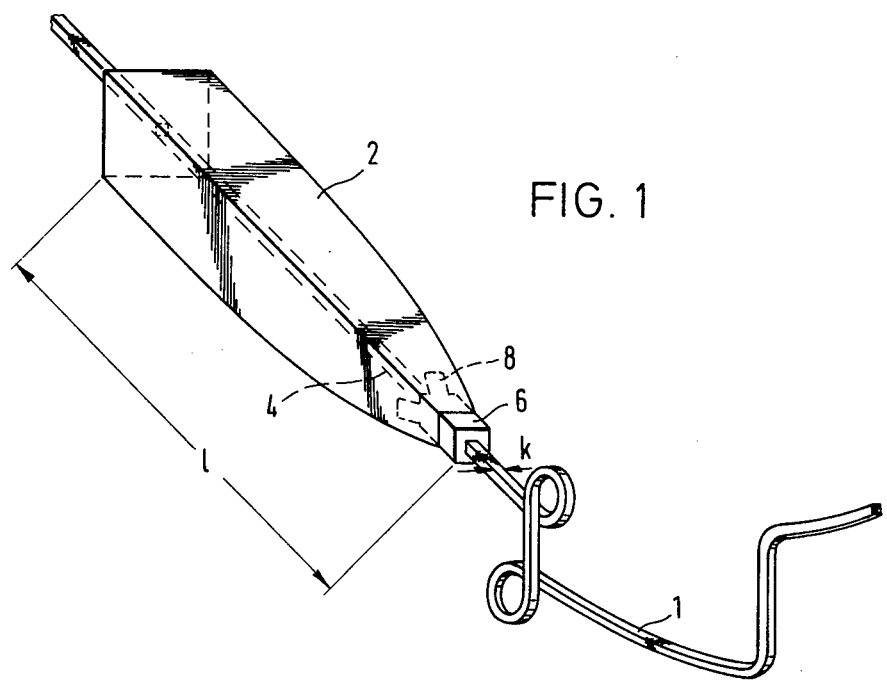
FIG. 1 is an inclined elevational view of an apparatus according to the invention in operating position.

FIG. 1 shows a partly completed bend 1 curved from a wire of square cross sectional area. As a rule, wires are used whose cross section is a square, such as shown in the figure. Yet it is also possible to use wires which have a rectangular cross section. The edge length of the square wire is designated K. That section of bend 1 which is to be curved as yet is located in a wire holder 2 of prismatic outside shape. Wire holder 2 has a central guide bore 4 which extends in the longitudinal direction of the wire holder and is adapted to the cross section of the square wire. The square wire protrudes from the rear end face of wire holder 2, not to be seen in the drawing. Wire holder 2 tapers toward its front end at which it is provided with a metal insert 6. This metal insert 6 has the shape of a square tube with an internal bore which again has exactly the same cross sectional outline as the square wire which it is to guide. The guide length of metal insert 6 is approximately eight to twelve times the edge length K of the square wire.

Metal insert 6 is embedded in wire holder 2 which is to consist of synthetic resin or metal. For improved mounting, metal insert 6 is formed with barbs 8. The overall length of wire holder 2 is designated 1 and corresponds approximately to a hundred times the edge length K of the square wire. The curvatures or torsions in the square wire to obtain the desired configurations are made directly in front of the front end of wire holder 2. In the embodiment shown this is approximately where the edge length of the square wire is marked by arrows. Every time the wire has been bent or twisted it can be pulled forward out of wire holder 2 by such a length that the location is reached at which the next curvature is to be made.

Figure 2:
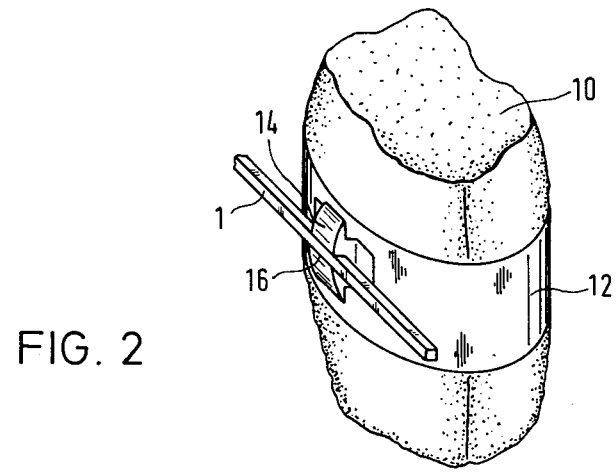
FIG. 2 is an inclined elevational partial view of the connection of a square bend to the crown of a tooth.

FIG. 2 is a diagrammatic presentation of the crown 10 of a tooth provided with a steel band 12 which includes a band fastener 14. In the band fastener 14 a square recess 16 is formed which is adapted exactly to the square cross section of bend 1. Thus bend 1 is seated accurately in band fastener 14. This fit also permits the transmission of torsional moments about the longitudinal axis of bend 1.

What is claimed is:

1. A method for tooth regulation through the application of force to a tooth through a band affixed thereto comprising the steps, of producing a bend in a square steel wire by means of a loop bending pliers, by securing a portion of the wire against torsion about its longitudinal axis in a holding device and leaving a portion of the wire in an unsupported condition extending from the holding device bending the unsupported portion to the desired curvature and subsequently fixing the bent wire in the band.

2. A method as claimed in claim 1, wherein said wire is secured against torsion about its longitudinal axis by being guided in a guide bore of the holding device, the cross sectional outline of conforming substantially to the cross sectional outline of the square wire.

3. An apparatus for carrying out the method as claimed in claim 1, wherein the holding device comprises a wire holder having a guide bore which is open at both ends and the cross sectional outline of which conforms to the cross sectional outline of the wire.

4. An apparatus as claimed in claim 3, wherein the fit between wire and bore is a sliding fit.

5. An apparatus as claimed in claim 3 or 4, wherein said wire holder has a prismatic outer shape and tapers toward one end.

6. An apparatus as claimed in claim 5, wherein the length of said wire holder corresponds approximately to a hundred times the greatest edge length of the wire cross section, while the height and width of said wire holder each correspond to approximately ten to twenty times the greatest edge length of the wire cross section.

7. An apparatus as claimed in claim 6, wherein said wire holder consists of synthetic resin, a similar non-deformable plastic, or metal.

8. An apparatus as claimed in claim 7, wherein a metal insert is provided at the tapering end of said wire holder to guide said wire.

9. An apparatus as claimed in claim 8, wherein said metal insert has a guide length corresponding to approximately eight to twelve times the greatest edge length of the wire cross section.

* * * * *